United States Patent
Roy et al.

(10) Patent No.: US 6,500,944 B2
(45) Date of Patent: *Dec. 31, 2002

(54) SULFURIZING REAGENT: 3-ARYL-1,2,4-DITHIAZOLINE-5-ONES

(75) Inventors: Saroj K. Roy, Acton, MA (US); Jin-Yan Tang, Shrewsbury, MA (US)

(73) Assignee: Avecia Biotechnology, Inc., Milford, MA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 10 days.

(21) Appl. No.: 08/895,136

(22) Filed: Jul. 16, 1997

(65) Prior Publication Data

US 2002/0010326 A1 Jan. 24, 2002

(51) Int. Cl.$^7$ .............................................. C07H 21/00
(52) U.S. Cl. ..................... 536/25.34; 536/25.3; 558/95; 548/129; 548/130
(58) Field of Search ............................. 536/25.3, 25.34; 548/129, 130; 530/345, 330, 331, 404; 558/95

(56) References Cited

U.S. PATENT DOCUMENTS 5,852,168 A * 12/1998 Barany et al. ............... 530/345

FOREIGN PATENT DOCUMENTS

EP  0 226 642  7/1987

OTHER PUBLICATIONS

PCT International Preliminary Examination Report for International Application No. PCT/US98/14687; Authorized Officer: Gallego, A.; Date of Completion of Report: Sep. 10, 1999 (7 pages).

Chemical Abstracts, vol. 93, No. 25, "Dithiazoles as fungicides", Abstract No. 232703e, Dec. 1980.

Xu, Qinghong, et al., 1996 Nucleic Acids Research, vol. 24, No. 9, "Use of 1,2,4–dithiazolidine–3,5–dione (DtsNH) and 3–ethoxy–1,2,4–dithiazoline–5–one (EDITH) for synthesis of phosphorothioate–containing oligodeoxyribonucleotides", pp. 1602–1607.

* cited by examiner

Primary Examiner—James O. Wilson
Assistant Examiner—Howard V. Owens, Jr.
(74) Attorney, Agent, or Firm—Hamilton, Brook, Smith & Reynolds, P.C.

(57) ABSTRACT

The invention relates to the chemical synthesis of oligonucleotides and to chemical entities useful in such synthesis. More particularly, the invention relates to sulfurization of the internucleotide linkages of oligonucleotides. The invention provides a process to synthesize new sulfur transfer reagents and a process for their use in sulfurizing oligonucleotides. The sulfur transfer reagents according to the invention are inexpensive to make, stable in storage and in solution, and highly efficient in sulfurization.

8 Claims, 7 Drawing Sheets

SULFURIZING REAGENT: 3-ARYL-1,2,4-DITHIAZOLINE-5-ONES

BACKGROUND OF THE INVENTION

1. Field of the Invention

The invention relates to the chemical synthesis of oligonucleotides and to chemical entities useful in such synthesis. More particularly, the invention relates to the synthesis of novel sulfur transfer reagents and to the sulfurization of the internucleotide linkages of oligonucleotides with the reagents.

2. Summary of the Related Art

Oligonucleotides have become indispensable tools in modern molecular biology, being used in a wide variety of techniques, ranging from diagnostic probing methods to PCR to antisense inhibition of gene expression. Oligonucleotide phosphorothioates are of considerable interest in nucleic acid research and are among the analogues tested as oligonucleotide therapeutics. Oligonucleotides phosphorothioates contain internucleotide linkages in which one of the nonbridging oxygen atoms of the phosphate group is replaced by a sulfur atom. This widespread use of oligonucleotides has led to an increasing demand for rapid, inexpensive, and efficient methods for synthesizing oligonucleotides.

The synthesis of oligonucleotides for antisense and diagnostic applications can now be routinely accomplished. See eg., *Methods in Molecular Biology, Vol 20: Protocols for Oligonucleotides and Analogs*, pp. 165–189 (S. Agrawal, ed., Humana Press, 1993); *Oligonucleotides and Analogues: A Practical Approach*, pp. 87–108 (F. Eckstein, ed., 1991); and Uhlmann and Peyman, *Chemical Reviews*, 90: 543–584 (1990); Agrawal and Iyer, *Curr. Op. in Biotech.* 6: 12 (1995); and *Antisense Research and Applications* (Crooke and Lebleu, eds., CRC Press, Boca Raton, 1993). Early synthetic approaches included phosphodiester and phosphotriester chemistries. Khorana et al., *J. Molec. Biol.* 72: 209 (1972) discloses phosphodiester chemistry for oligonucleotide synthesis. Reese, *Tetrahedron Lett.* 34: 3143–3179 (1978), discloses phosphotriester chemistry for synthesis of oligonucleotides and polynucleotides. These early approaches have largely given way to the more efficient phosphoramidite and H-phosphonate approaches to automated synthesis. Beaucage and Carruthers, *Tetrahedron Lett.* 22: 1859–1862 (1981), discloses the use of deoxynucleoside phosphoramidites in polynucleotide synthesis. Agrawal and Zamecnik, U.S. Pat. No. 5,149,798 (1992), discloses optimized synthesis of oligonucleotides by the H-phosphonate approach.

These latter approaches have been used to synthesize oligonucleotides having a variety of modified internucleotide linkages. Agrawal and Goodchild, *Tetrahedron Lett.* 28: 3539–3542 (1987), teaches synthesis of oligonucleotide methylphosphonates using phosphoramidite chemistry. Connolly et al., *Biochemistry* 23: 3443 (1984), discloses synthesis of oligonucleotide phosphorothioates using phosphoramidite chemistry. Jager et al., *Biochemistry* 27: 7237 (1988), discloses synthesis of oligonucleotide phosphoramidates using phosphoramidite chemistry. Agrawal et al., *Proc. Natl. Acad. Sci. USA* 85: 7079–7083 (1988), discloses synthesis of oligonucleotide phosphoramidates and phosphorothioates using H-phosphonate chemistry.

Solid phase synthesis of oligonucleotides by each of the foregoing processes involves the same generalized protocol. Briefly, this approach comprises anchoring the 3'-most nucleoside to a solid support functionalized with amino and/or hydroxyl moieties and subsequently adding the additional nucleosides in stepwise fashion. Internucleoside linkages are formed between the 3' functional group of the incoming nucleoside and the 5' hydroxyl group of the 5'-most nucleoside of the nascent, support-bound oligonucleotide. In the phosphoramidite approach, the internucleoside linkage is a phosphite linkage, whereas in the H-phosphonate approach, it is an H-phosphonate internucleoside linkage. To create the sulfur-containing phosphorothioate internucleoside linkage, the phosphite or H-phosphonate linkage must be oxidized by an appropriate sulfur transfer reagent. In the H-phosphonate approach, this sulfurization is carried out on all of the H-phosphonate linkages in a single step following the completion of oligonucleotide chain assembly, typically using elemental sulfur in a mixed solvent, such as $CS_2$/pyridine. In contrast, the phosphoramidite approach allows stepwise sulfurization to take place after each coupling, thereby providing the capability to control the state of each linkage in a site-specific manner. Based on superior coupling efficiency, as well as the capacity to control the state of each linkage in a site-specific manner, the phosphoramidite approach appears to offer advantages.

Refinement of methodologies is still required, however, particularly when making a transition to large-scale synthesis (10 $\mu$mol to 1 mmol and higher). See Padmapriya et al., *Antisense Res. Dev.* 4: 185 (1994). Several modifications of the standard phosphoramidite processes have already been reported to facilitate the synthesis (Padmapriya et al., supra; Ravikumar et al., *Tetrahedron* 50: 9255 (1994); Theisen et al., *Nucleosides & Nucleotides* 12: 43 (1994); and Iyer et al., *Nucleosides & Nucleotides* 14: 1349 (1995)) and isolation (Kuijpers et al., *Nucl. Acids Res.* 18: 5197 (1990); and Reddy et al., *Tetrahedron Lett.* 35: 4311 (1994)) of oligonucleotides.

It is imperative that an efficient sulfur transfer reagent is used for the synthesis of oligonucleotide phosphorothioates via the phosphoroamidite approach. Elemental sulfur is not efficient due to poor solubility and slow sulfurization reaction. A number of more efficient sulfurizing reagents have been reported in recent years. These include phenylacetyl disulfide, (Kamer et al., *Tetrahedron Lett.* 30: 6757–6760 (1989)), H-1,2-benzodithiol-3-one-1,1-dioxide (Beaucage reagent)(Iyer et al., *J. Org. Chem.* 55: 4693–4699 (1990)), tetraethylthiuram disulfide (TETD)(Vu et al., *Tetrahedron Lett.* 32: 3005–3008 (1991)), dibenzoyl tetrasulfide (Rao et al., *Tetrahedron Lett.* 33: 4839–4842 (1992)), bis(O,O-diisopropoxyphosphinothioyl) disulfide (S-Tetra)(Stec et al., *Tetrahedron Lett.* 33: 5317–5320 (1993)), benzyltriethylammonium tetrathiomolybate (BTTM) (Rao et al., *Tetrahedron Lett.* 35: 6741–6744 (1994)), bis(p-toluenesulfonyl) disulfide (Effimov et al., *Nucl. Acids Res.* 23: 4029–4033 (1995)), 3-ethoxy-1,2,4-dithiazoline-5-one (EDITH)(Xu et al., *Nucleic Acid Res.* 24:1602–1607 (1996)), and 1,2,4-dithiazolidine-3,5-dione (DtsNH)(Xu et al., *Nucleic Acid Res.* 24:1602–1607 (1996)). Both Beaucage reagent and TETD are commercially available. Beaucage reagent has been widely used, however, its synthesis and stability are not optimal. In addition, the by-product formed by Beaucage reagent during sulfurization, 3H-2,1-benzoxanthiolan-3-one-1-oxide, is a potential oxidizing agent that can lead to undesired phosphodiester linkages under certain conditions. Therefore, its application in large-scale synthesis of oligonucleotide phosphorothioates may not be particularly suitable. We report the novel preparation of 3-phenyl-1,2,4-dithiazoline-5-one as a potential alternative sulfurizing reagent.

There is, therefore, a continuing need to develop new sulfur transfer reagents and processes for sulfurizing oligonucleotides. Ideally, such sulfur transfer reagents should be inexpensive to make, stable in storage and in solution, and highly efficient in sulfurization.

BRIEF SUMMARY OF THE INVENTION

The invention provides new sulfur transfer reagents, 3-aryl-1,2,4-dithiazoline-5-ones, for use in sulfurizing oligonucleotides. The sulfur transfer reagents according to the invention are inexpensive to make, stable in storage and in solution for thirty days, and highly efficient in sulfurization.

In a first aspect, the invention provides novel sulfur transfer reagents having the general structure (1)

(1)

wherein R is or any substituted heterocyclic or substituted aromatic group. The sulfur transfer reagent 3-phenyl-1,2,4-dithiazoline-5-one is a particularly preferred embodiment of the invention and has the structure (2)

(2)

A second aspect provides for the synthesis of novel sulfur transfer reagents according to the invention.

In a third aspect, the invention provides a novel process for adding a sulfur group to an internucleotide linkage of an oligonucleotide using the novel sulfur transfer reagent according to the invention.

DETAILED DESCRIPTION OF THE PREFERRED EMBODIMENTS

The invention relates to the chemical synthesis of oligonucleotides and to chemical entities useful in such synthesis. More particularly, the invention relates to sulfurization of the internucleotide linkages of oligonucleotides. The patents and publications identified in this specification are within the knowledge of those skilled in this field and are hereby incorporated by reference in their entirety.

The invention provides a process to synthesize new sulfur transfer reagents and a process for their use in sulfurizing oligonucleotides. The sulfur transfer reagents according to the invention are inexpensive to make, stable in storage and in solution, and highly efficient in sulfurization.

In a first aspect, the invention provides novel sulfur transfer reagents having the general structure (1):

(1)

wherein R is or any substituted heterocyclic or substituted aromatic group.

A preferred embodiment of these novel sulfur transfer reagents is 3-phenyl-1,2,4-dithiazoline-5-one having the structure (2):

(2)

In a second aspect, the novel sulfur transfer reagents according to structure (1) can be easily synthesized in a one-step reaction according to Scheme 1 at a yield of more than 75% at a 10 gram scale.

Scheme 1

The mechanism of this one-step reaction may be explained as a nucleophilic attack of the sulfur of the thiocarbonyl group to the sulfenyl chloride, which subsequently provides chlorocarbonyl benzalimine disulfane and then cyclizes to dithiazolinone by a nucleophilic attack to the carbonyl group.

Stability and solubility studies of the sulfur transfer reagents were performed. The compound 3-phenyl-1,2,4-dithiazoline-5-one according to the invention is stable in $CH_3CN$ for more than thirty days. No precipitation occurred during the testing period. The stability of the compound was checked by HPLC and $^1$H-NMR.

Furthermore, 3-phenyl-1,2,4-dithiazoline-5-one is highly soluble in $CH_3CN$, which is the preferred solvent for oligonucleotide synthesis.

Accordingly, it has been demonstrated that the oligonucleotide phosphorothioates can be efficiently prepared by solid-phase phosphoramidite approach using 3-phenyl-1,2, 4-dithiazoline-5-one. Due to its high efficiency for transferring sulfur atoms, as well as its high stability, high solubility, and low cost for preparation, 3-phenyl-1,2,4-dithiazoline-5-one according to the invention can be considered an advantageous alternative to Beaucage reagent and EDITH, especially in large-scale preparation of oligonucleotide phosphorothioates.

In another aspect, the invention provides a novel process for adding a sulfur atom to an internucleotide linkage of an oligonucleotide using 3-aryl-1,2,4-dithiazoline-5-ones. In a preferred embodiment, the novel process according to the invention comprises contacting an oligonucleotide having at least one sulfurizable internucleotide linkage with the novel 3-aryl-1,2,4-dithiazoline-5-one sulfur transfer reagent, 3-phenyl 1,2,4-dithiazoline-5-one, for a time sufficient for sulfurization of the sulfurizable internucleotide linkage(s) to occur. Each sulfurizable internucleotide linkage preferably contains a phosphorous (III) atom.

In a particularly preferred embodiment, the sulfurizable internucleotide linkage is a phosphite, thiophosphite, H-phosphonate, thio-H-phosphonate, or alkylphosphite (especially methylphosphite) internucleotide linkage. Preferably, the sulfurization reaction would be allowed to proceed to a sulfur transfer efficiency greater than that expected for the prior art compounds, as measured by $^{31}$P-NMR. In typical synthetic conditions, such efficiency is achieved within from about 1 to about 5 minutes reaction time with the novel transfer reagent. Also, the reaction usually takes place in $CH_3CN$ solution For purposes of this aspect of the invention, the term oligonucleotide includes linear polymers of two or more natural deoxyribonucleotide, ribonucleotide, or 2'-O-substituted ribonucleotide monomers, or any combination thereof. The term oligonucleotide also encompasses such polymers having chemically modified bases or sugars and/or non-nucleosidic analogs linked by phosphodiester bonds or analogs thereof ranging in size from a few monomeric units, e.g., 2–3, to several hundred monomeric units and/or having additional substituents, including without limitation lipophilic groups, intercalating agents, diamines and adamantane. In particular, oligonucleotides may also include non-natural oligomers having phosphorous-containing internucleoside linkages whose phosphorous (III) precursors are amenable to sulfurization (See, e.g., Takeshita et al., *J. Biol. Chem* 282: 10171–10179 (1987)). For purposes of the invention, the term 2'-O-substituted means substitution of the 2' position of the pentose moiety with an —O-lower alkyl group containing 1–6 saturated or unsaturated carbon atoms, or with an —O-aryl or allyl group having 2–6 carbon atoms, wherein such alkyl, aryl or allyl group may be unsubstituted or may be substituted, eg., with halogen, hydroxy, trifluoromethyl, cyano, nitro, acyl, acyloxy, alkoxy, carboxy, carbalkoxy, or amino groups; or with a hydroxy, an amino or a halogen group, but not with a 2'-H group. Such oligonucleotides may include any of the internucleoside linkages which are known in the art, including without limitation phosphorothioate, phosphorodithioate, alkylphosphonate (especially methylphosphonate), phosphoramidate, amide (PNA), carbamate, and alkylphosphonothioate linkages. In a preferred embodiment, the oligonucleotide is bound to a solid support, but such oligonucleotides may be sulfurized in solution phase as well.

Figure 4:
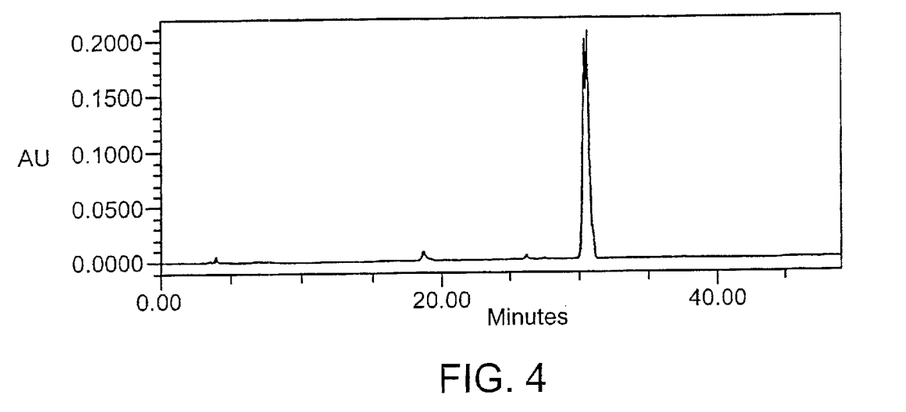
FIG. 4 shows the HPLC of DMT protected T—T phosphorothioate dimer synthesized with 3-phenyl-1,2,4-dithiazoline-5-one as a sulfur transfer reagent at 1.2 equiv. of 0.1 M solution.
Figure 5:
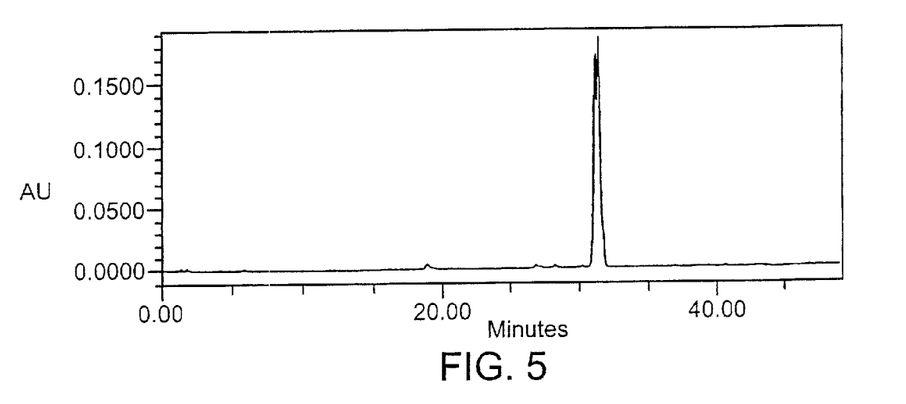
FIG. 5 shows the HPLC of DMT protected T—T phosphorothioate dimer synthesized with 3-phenyl-1,2,4-dithiazoline-5-one as a sulfur transfer reagent at 2 equiv. of 0.1 M solution.
Figure 6:
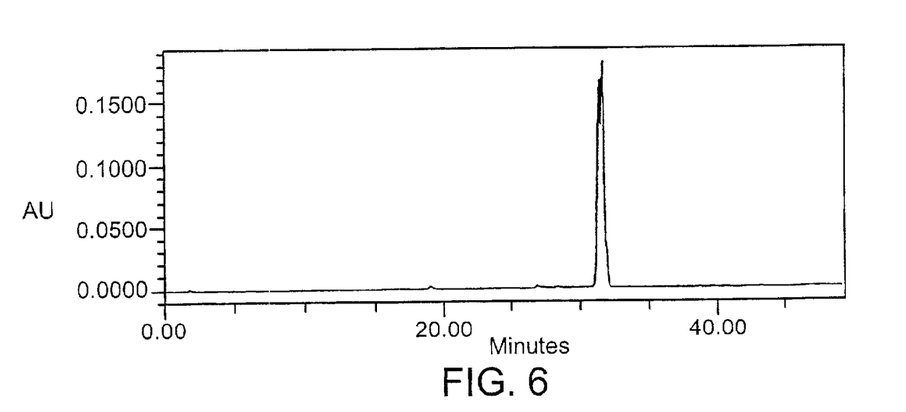
FIG. 6 shows the HPLC of DMT protected T—T phosphorothioate dimer synthesized with 3-phenyl-1,2,4-dithiazoline-5-one as a sulfur transfer reagent at 4 equiv. of 0.1 M solution.

The efficiency of this new sulfur transfer reagent was first evaluated by solid-phase synthesis of dinucleotide phosphorothioate, 5'-DMT-TT-OH-3'. Synthesis was performed at 1.0 μmol scale using the standard phosphorothioate protocol ("THIO 1 μmol"). The dinucleotide phosphorothioate was analyzed by reverse-phase HPLC. The results show that a better than 99.8% sulfur transfer efficiency was achieved using 3-phenyl-1,2,4-dithiazoline-5-one. (FIGS. 4–6.)

EXAMPLES

The following examples are intended to further illustrate certain preferred embodiments of the invention and are not intended to be limiting in nature.

In general, anhydrous $CH_3CN$ was purchased from J. T. Baker Inc. (Phillipsburg, N.J.). dT-CPG, 5'-DMT-thymidine cyanoethyl phosphoramidite, Cap A, Cap B, activator, oxidizing and deblock solutions were purchased from PerSeptive Biosystems, (Framingham, Mass.). Beaucage reagent (3H-1,2-benzodithiol-3-one-1,1-dioxide) was purchased from R. I. Chemical (Orange, Calif.). All other chemicals were purchased from Aldrich. $^{31}$P-NMR spectra (121.65 MHz) and $^1$H-NMR spectra (300 MHz) were recorded on a Varian UNITY 300 (the chemical shift was correlated to 85% $H_3PO_4$ and tetramethylsilane, respectively). Dinucleotide and oligonucleotide syntheses were performed on an automated nucleic acid synthesizer (8909 EXPEDITE™, Millipore, Bedford, Mass.). Reverse phase HPLC was performed on a Waters 600E pump with a Waters 440 absorbance detector, Waters 746 integrator, and a Nova-Pak C18 (3.9×150 mm) column, using a linear gradient of $CH_3CN$-aqueous $NH_4OAc$ (0.1 M) (4:1) and 0.1 M aqueous $NH_4OAc$ from 1:9 to 3:2 over a period of 40 min, flow rate 2 mL/min, detection at 260 nm. Ion-exchange HPLC analyses were performed on a Beckman System Gold 126 with a Beckman 166 absorbance detector on a NUCEOPAC PA-100 column (4×50 mm) using a linear gradient of Buffer A (25 mM of Tris-HCl and 1 mM EDTA, $CH_3CN$, pH=8) and Buffer B (2 M NaCl and buffer A) from 100% Buffer A to 100% Buffer B over a period of 5 min, then maintained at 100% Buffer B for 3 min, flow rate 2 ml/min, detection at 254 nm. Capillary electrophoresis was performed on a Beckman P/ACE System 5010. Samples were injected for 5 seconds and analyzed for 40 min.

Example 1

Synthesis of 3-phenyl-1,2,4-dithiazoline-5-one

Figures 1, 1A:
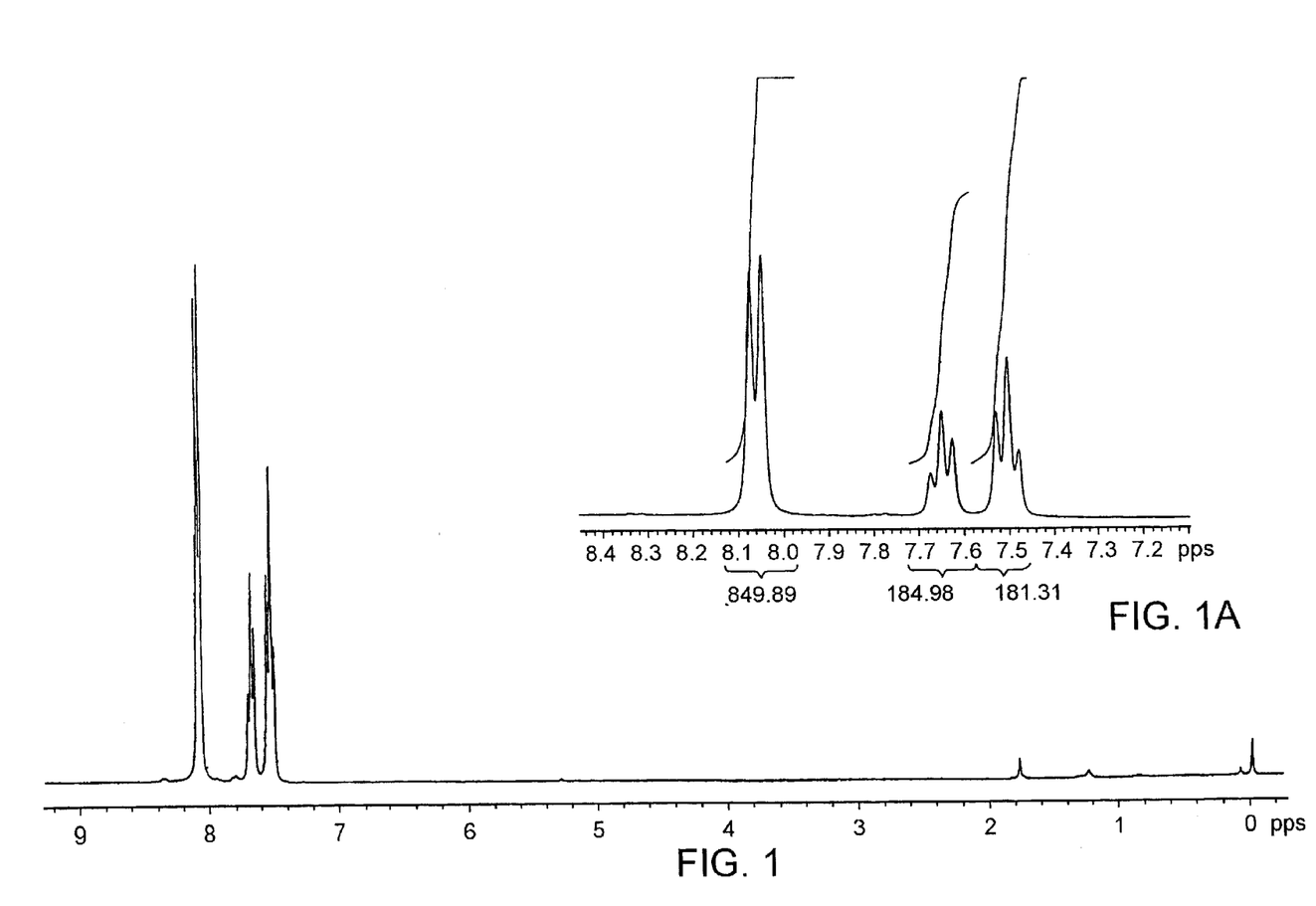
FIG. 1 shows the $^1$H-NMR spectrum of 3-phenyl-1,2,4-dithiazoline-5-one.
Figure 2:
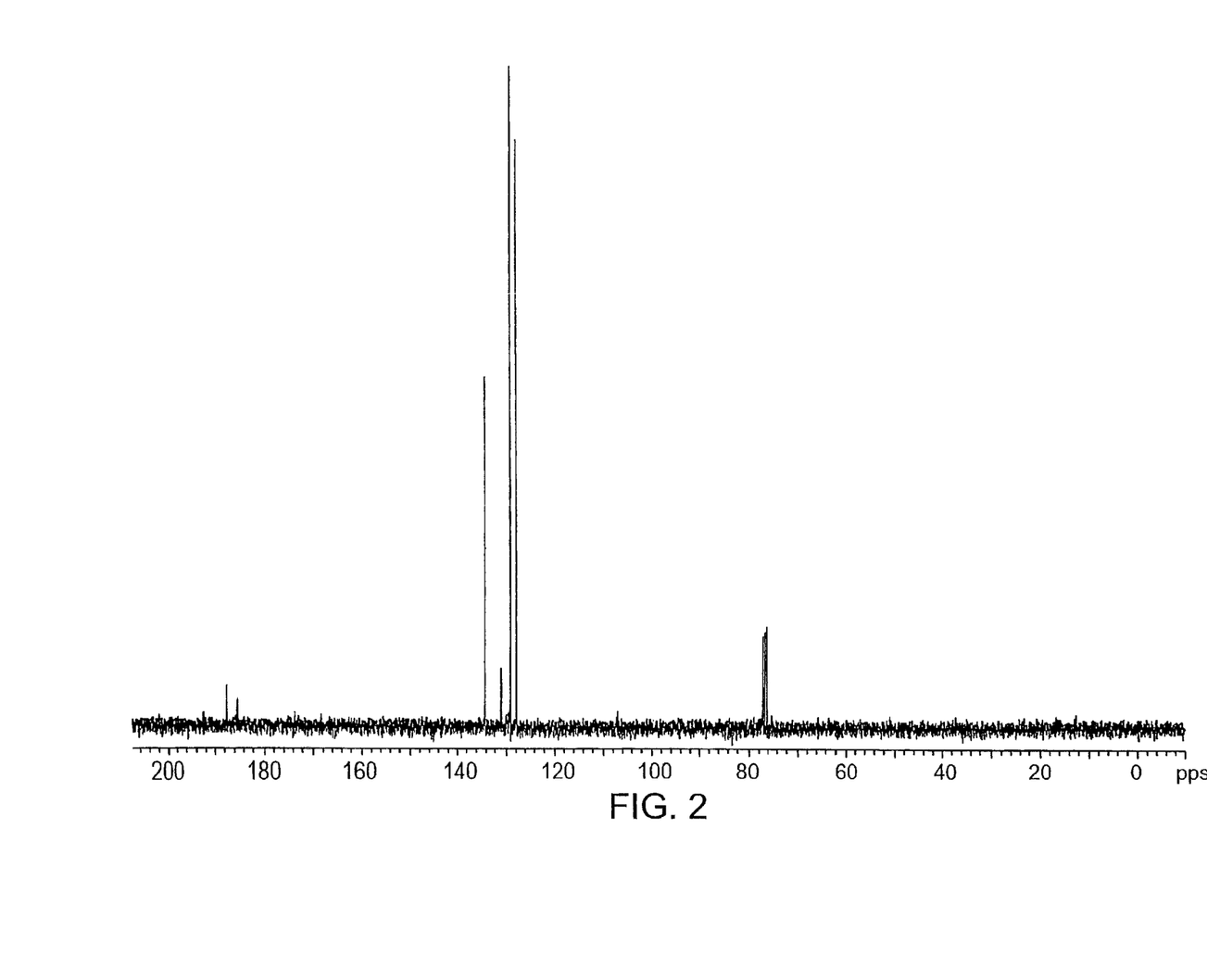
FIG. 2 shows the $^{13}$C-NMR spectrum of 3-phenyl-1,2,4-dithiazoline-5-one.
Figure 3A:
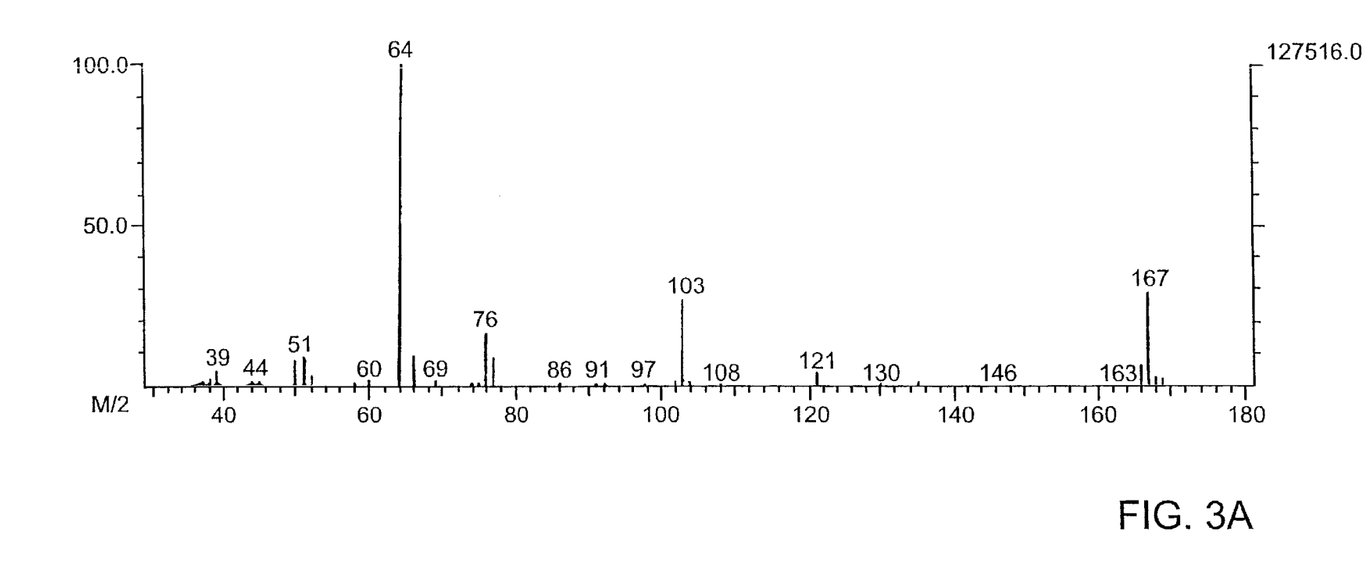
FIG. 3 shows the mass spectrum of 3-phenyl-1,2,4-dithiazoline-5-one.
Figure 3B:
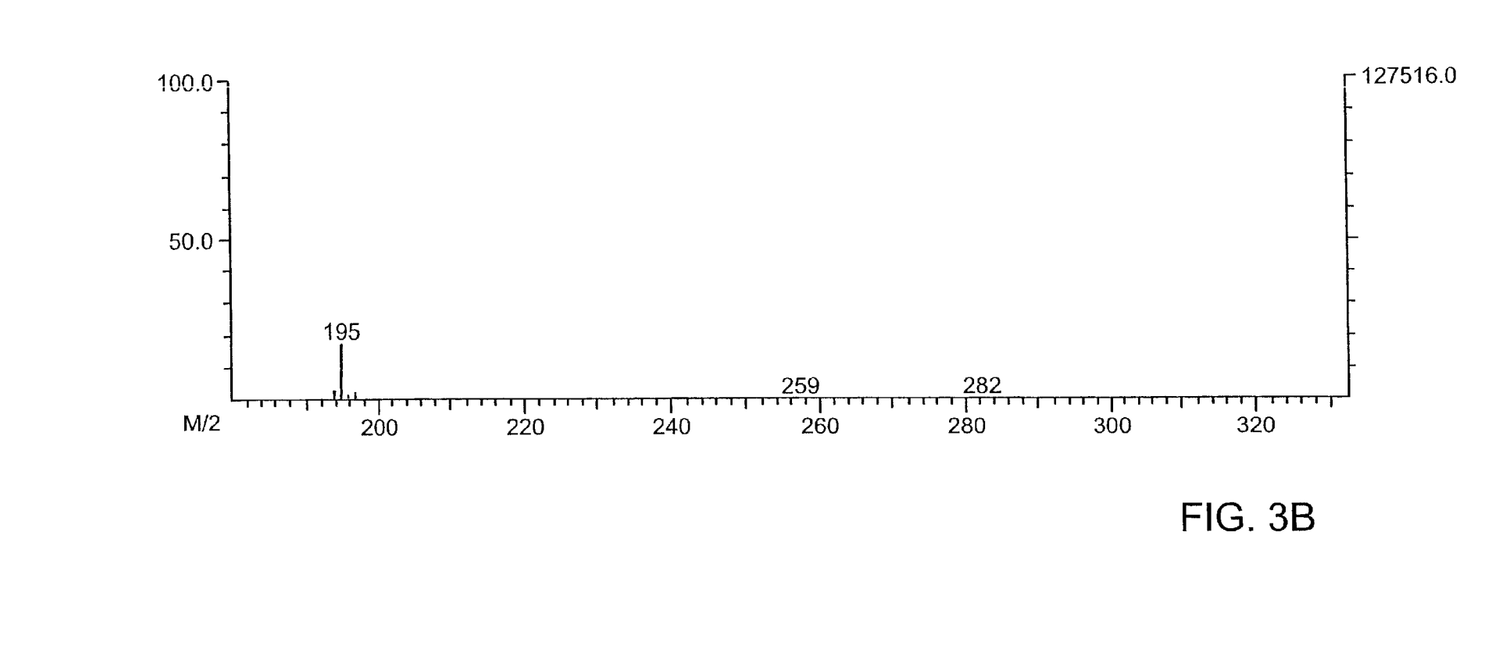

All the glassware were dried in the preheated oven prior to the reaction for two hours at 200° C. A 500 ml three neck round bottom flask was equipped with magnetic bar, thermometer, pressure equalizing funnel and a positive inflow of argon. The assembly was placed on to the magnetic stirrer having ice bath. Chlorocarbonyl sulfenyl chloride (9.55 grams, 72.87 mmol) was transferred to the reaction flask. 100 ml of $CH_3CN$ was also added to the flask. The mixture was cooled down to 10° C. Thiobenzamide (10 grams, 72.87 mmol) was dissolved in a separate flask using 80 ml of $CH_3CN$ and diisopropylethylamine (18.84 gm, 145.76 mmol). This solution was transferred to the pressure equalizing funnel. The thiobenzamide solution was added slowly to the reaction flask. The temperature of the flask raised to 12–15° C. The mixture was stirred for 30 min. at 5–10° C. The disappearance of the starting material and formation of two isomeric nonpolar spots was observed on TLC. The reaction mixture was filtered through a sintered funnel. The filtrate was rotaevaporated to dryness and left on high vacuum for two hours. The solid was crystallized with a mixture of hexanes and ethyl acetate in a ratio of 95:5, respectively. The upper nonpolar spot on the TLC was left behind in the mother liquor and characterized as 3,5-diphenyl-1,2,4-thiadiazole. The crystals of 3-phenyl-1,2,4-dithiazoline-5-one were light yellow in color and the recovery was 9.25 gm (65%). The yield of the crude mix was 75%. The structure of 3-phenyl-1,2,4-dithiazoline-5-one was confirmed by $^1$H-NMR (FIG. 1), $^{13}$C-NMR (FIG. 2), mass spectrometry (FIG. 3) and elemental analysis.

Example 2

Stability and Solubility Studies of 3-phenyl-1,2,4-dithiazoline-5-one in $CH_3CN$ The solubility and stability studies were carried out in $CH_3CN$ at 25° C. The saturated solution was dried, and the solubility was determined by the weight of the testing compounds in the exact volume of testing solution. The stability was determined based on either TLC or HPLC and $^1$H-NMR analyses.

Example 3

Synthesis of Dinucleotide Phosphorothioate

Dimer was assembled on a PerSeptive DNA/RNA (Millipore 8909 Expedite™, Millipore, Bedford, Mass.) on a 1 μmol scale using the synthesis protocol "THIO 1 μmol" (Expedite software version 1.01), starting from DMT-T-CPG (500 Å, loading: 60 μmol/g). The sulfurizing reagent was prepared in $CH_3CN$ at a concentration of 0.1 M unless specified. Sulfurization was carried out using 1.2 equiv., 2 equiv., and 4 equiv. of 3-phenyl-1,2,4-dithiazoline-5-one for a 1 min. reaction. Final cleavage was carried out by treatment using concentrated ammonium hydroxide (1 μmol/1 mL) at 25° C. for 1 h. CPG and other insoluble residues were removed by filtration, and the ammonium hydroxide solution was dried by lyophilization. HPLC analysis was carried out using a linear gradient of 0.1 M aqueous $NH_4OAc$ and $CH_3CN$-aqueous $NH_4OAc$ (0.1 M) (4:1) from 1:9 to 3:2 over a period of 40 min, flow rate 1.0 mL/min, detection at 260 nm. 5'-DMT-T(P=S)-T-OH-3' diastereomers were eluted at approximately $t_R$=31.6 min. The corresponding P=O dimer was eluted at approximately $t_R$=28.4 min. (FIGS. 4–6.) The P=O impurity was less than 0.2% in each case.

Example 4

Synthesis of a 25 mer Oligonucleotide Phosphorothioate on 1 μmol Scale

Figure 7:
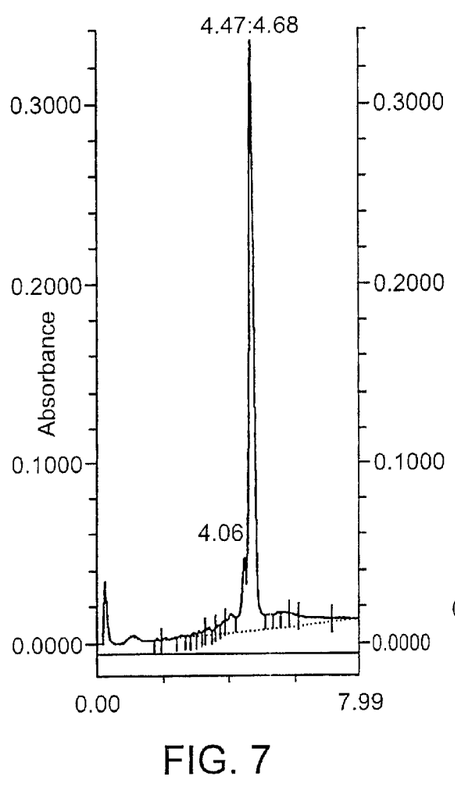
FIG. 7 shows the HPLC of a 25 mer oligonucleotide phosphorothioate synthesized with 3-phenyl-1,2,4-dithiazoline-5-one as a sulfur transfer reagent at 1.2 equiv. of 0.1 M solution.
Figure 8:
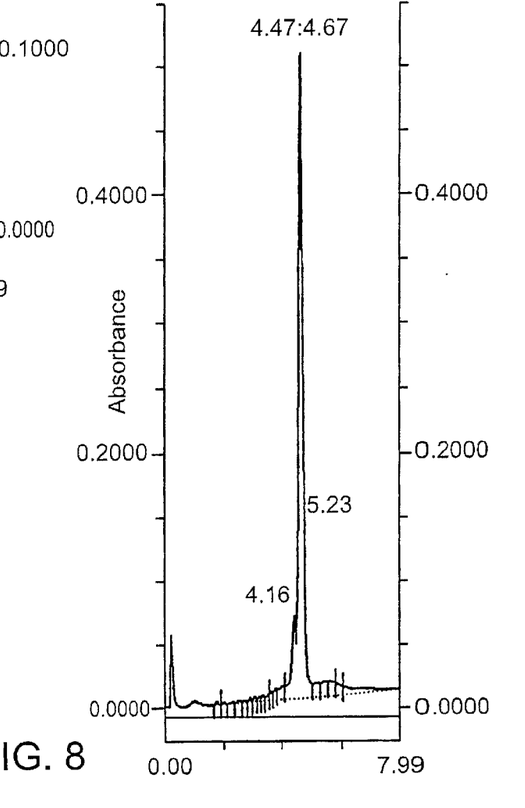
FIG. 8 shows the HPLC of a 25 mer oligonucleotide phosphorothioate synthesized with 3-phenyl-1,2,4-dithiazoline-5-one as a sulfur transfer reagent at 2.5 equiv. of 0.1 M solution.

A 25 mer oligonucleotide (SEQ. ID NO. 1) was synthesized on (EXPEDITE™, Millipore 8900, Bedford, Mass.) on a 1 μmol scale using the synthesis protocol "THIO 1 μmol" (EXPEDITE™ software version 1.01), starting from DMT-T-CPG (500 Å, loading; 60 μmol/gm). The sulfurizing reagent was prepared in $CH_3CN$ at a concentration of 0.1 M unless specified. Sulfurization was carried out using 1.2 equiv. and 2.5 equiv. of 3-phenyl-1,2,4-dithiazoline-5-one for 1 min. reaction. Final cleavage was carried out by treatment using concentrated ammonium hydroxide (1 μmol/ml) at 55° C. for 6 hour. CPG and other insoluble residues were removed by filtration, and the ammonium hydroxide solution was dried by lyophilization. An exchange HPLC analysis was carried out using a linear gradient of Buffer A (1 mM EDTA, 25 mM Tris (pH 8.0); $CH_3CN$ (9:1)) and Buffer B (1 mM EDTA, 25 mM Tris (pH 8.0), 2.5 M $NH_4Cl$; $CH_3CN$ (9:1)) from 80% Buffer A:20% Buffer B to 100% Buffer B over a period of 3 min, flow rate 2 ml/min, detection at 256 nm. The sulfurized 25 mer oligonucleotide was eluted at approximately $t_R$=4.47 min. The corresponding P=O impurity was eluted at approximately $t_R$=4.07 min. (FIGS. 7 and 8.) The P=O impurity was less than 0.3% in each case.

Example 5

Figure 9:
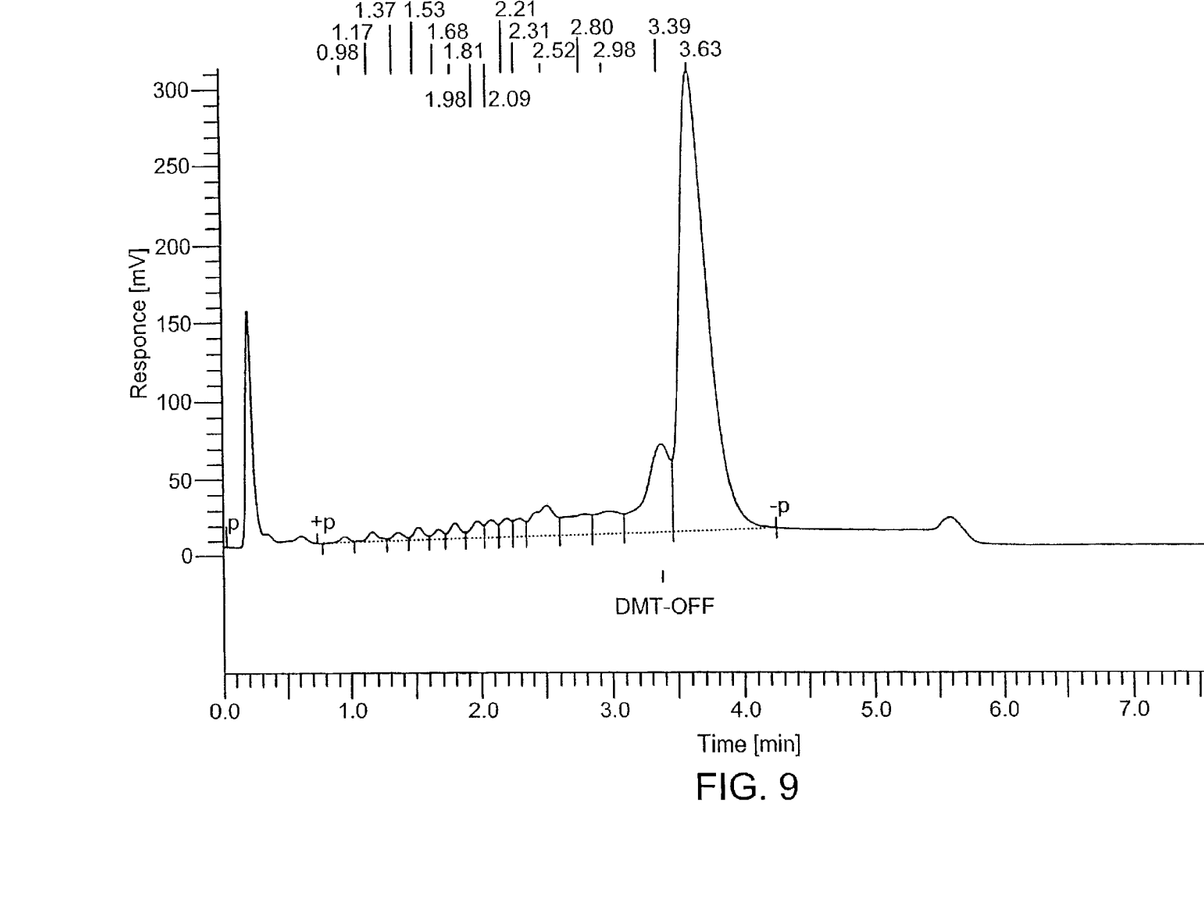
FIG. 9 shows the HPLC of a 25 mer oligonucleotide phosphorothioate synthesized with 3-phenyl-1,2,4-dithiazoline-5-one as a sulfur transfer reagent at 3.0 equiv. of 0.1 M solution.

Synthesis of a 25 mer Oligonucleotide Phosphorothioate on a 200 μmol scale A 25 mer oligonucleotide (SEQ ID NO:1) was synthesized on (Oligo Pilot II, Pharmacia Biotech, Piscataway, N.J.) on a 200 μmol scale using the synthesis software Unicorn OS V1.10, starting from DMT-T-PG (500 Å, loading 90 μmol/gm). The sulfurizing reagent was prepared in $CH_3CN$ at a concentration carried out using 3 equiv. of 3-phenyl-1,2,4-dithiazoline-5-one for a 1 min. reaction. Final cleavage was carried out by treatment using concentrated ammonium hydroxide (1 μmol/ml) at 55° C. for 6 hours. CPG and other insoluble residues were removed by filtration, and the ammonium hydroxide solution was dried by using a linear gradient of 25 mmol Tris, 1 mmol EDTA, $CH_3CN$ (9:1), 2.5M $NH_4Cl$; 25 mmol Tris, 1 mmol EDTA and $CH_3CN$ (9:1) over a period of 10 min, flow rate 2.0 ml/min, detection at 270 mm. The 25 mer oligonucleotide phosphorothioate was eluted at approximately $t_R$=3.63 min. The corresponding P=O impurity eluted at approximately $T_R$=3.39 min. (FIG. 9). The P=O impurity was less than 0.2%.

What we claim:

1. A process for adding a sulfur group to an internucleotide linkage of an oligonucleotide, the process comprising contacting an oligonucleotide having at least one sulfurizable internucleotide linkage with a sulfur transfer reagent for a time sufficient for sulfurization of the sulfurizable internucleotide linkage to occur, wherein the sulfur transfer reagent is represented by the following structural formula:

wherein R is phenyl, substituted phenyl, pyridyl or substituted pyridyl.

2. The process according to claim 1, wherein each sulfurizable internucleotide linkage contains a phosphorous (III) atom.

3. The process according to claim 2, wherein the sulfurizable internucleotide linkage is a phosphite, thiophosphite, H-phosphonate, thio-H-phosphonate, or alkylphosphite internucleotide linkage.

4. The process according to claim 3, wherein the sulfurization reaction is allowed to proceed from about 1 to about 5 minutes.

5. A process for adding a sulfur group to an internucleotide linkage of an oligonucleotide, the process comprising contacting an oligonucleotide having at least one sulfurizable internucleotide linkage with a sulfur transfer reagent for a time sufficient for sulfurization of the sulfurizable internucleotide linkage to occur, wherein the sulfur transfer reagent is represented by the following structural formula:

wherein R is phenyl.

6. The process according to claim 5, wherein each sulfurizable internucleotide linkage contains a phosphorous (III) atom.

7. The process according to claim 6, wherein the sulfurizable internucleotide linkage is a phosphite, thiophosphite, H-phosphonate, thio-H-phosphonate, or alkylphosphite internucleotide linkage.

8. The process according to claim 7, wherein the sulfurization reaction is allowed to proceed from about 1 to about 5 minutes.

* * * * *